United States Patent [19]

Carter

[11] Patent Number: 5,258,369
[45] Date of Patent: * Nov. 2, 1993

[54] TREATMENT OF CHRONIC CEREBRAL DYSFUNCTION BY DSRNA METHODOLOGY

[75] Inventor: William A. Carter, Birchrunville, Pa.

[73] Assignee: HEM Pharmaceuticals Corporation, Rockville, Md.

[*] Notice: The portion of the term of this patent subsequent to Aug. 21, 2007 has been disclaimed.

[21] Appl. No.: 899,004

[22] Filed: Jun. 15, 1992

Related U.S. Application Data

[63] Continuation-in-part of Ser. No. 967,579, Oct. 27, 1992, which is a continuation of Ser. No. 713,003, Jun. 10, 1991, abandoned, which is a continuation of Ser. No. 560,273, Jul. 30, 1990, abandoned, which is a continuation of Ser. No. 421,596, Oct. 16, 1989, abandoned, which is a continuation of Ser. No. 237,019, Aug. 29, 1988, abandoned.

[51] Int. Cl.$^5$ ............................................. A01N 43/04
[52] U.S. Cl. ........................................ 514/44; 514/49; 514/50
[58] Field of Search .................. 435/6; 514/44, 49, 50

[56] References Cited

FOREIGN PATENT DOCUMENTS 0306347 3/1989 European Pat. Off. .

Primary Examiner—Christine M. Nucker
Assistant Examiner—Jeffrey Stucker
Attorney, Agent, or Firm—Nixon & Vanderhye

[57] ABSTRACT

Patients having chronic fatigue syndrome having chronic cerebral dysfunction, as characterized by memory lapses occasional seizures and loss of cognitive functions are treated with a dsRNA such as rI·r(C$_{11-14}$,U) to improve the patient's clinical condition.

10 Claims, No Drawings

TREATMENT OF CHRONIC CEREBRAL DYSFUNCTION BY DSRNA METHODOLOGY

CROSS REFERENCE TO RELATED APPLICATIONS

This application is a continuation-in-part of earlier application Ser. No. 07/967,579, filed Oct. 27, 1992, pending which in turn is a continuation of Ser. No. 07/713,003, filed Jun. 10, 1991, abandoned, which in turn is a continuation of Ser. No. 07/560,273, filed Jul. 30, 1990, abandoned which is a continuation of Ser. No. 07/421,596, filed Oct. 16, 1989, abandoned which is a continuation of Ser. No. 07/237,019, filed Aug. 29, 1988, abandoned.

This invention relates to a method of treating a patient suffering from chronic fatigue syndrome and having chronic cerebral dysfunction, comprising administering to that patient an amount of dsRNA sufficient to improve the patient's clinical condition. The chronic cerebral dysfunction is evidenced by one or more of: partial loss of cognitive functions, impaired attention and abstraction ability, memory loss, immunological derangement in the natural killer cell function or phenotype, or both, or an enzymatic deficiency in the 2'-5'A pathway in the patient's peripheral blood cells.

The patients described in this application are a subset of patients meeting the criteria of chronic fatigue syndrome (CFS) as specifically advanced by a health branch of the U.S. government, namely the Centers for Disease Control (CDC), Altanta, Ga., described by Holmes et al., "Chronic Fatigue Syndrome: A Working Case Definition", Annals of Internal Medicine, vol. 108, pp. 387–389, 1988. Holmes et al. specifically describes a subset of patients (p. 389) manifesting "forgetfulness . . . confusion, difficulty thinking, inability to concentrate . . ."

In this invention, I identified a subset of CFS patients in which the above-mentioned cerebral dysfunctions were more debilitating than the fatigue itself, hence the more scientifically accurate term or identifier of "chronic cerebral dysfunction" is used herein and is intended to encompass the symptomatology of chronic "forgetfulness, confusion, difficulty thinking, etc." Indeed, the data reported hereinbelow evidences an actual deterioration in raw intelligence scores. These cerebral dysfunctions were ameliorated by the exogenous mismatched dsRNA infusions.

SUMMARY OF THE INVENTION

A group of patients suffering from an organic brain syndrome characterized by cerebral dysfunction were studied, some for more than 15 months. Following an infectious-like episode, they developed a novel post-infectious immune dysfunction characterized by progressive mental deterioration, associated with memory lapses, occasional seizures and loss of higher mental abilities (the so-called cognitive functions). Magnetic Resonance Imaging (MRI) of the brain, performed on patients complaining of cognitive problems, showed a variety of abnormalities of high signal intensities, including large patchy areas consistent with edema or demyelination. Peripheral blood cells showed enzymatic deficiencies in a novel antiviral pathway termed the double-stranded (ds) RNA linked 2-5 A/RNase L pathway. Treatment with an exogenous source of dsRNA caused improvement in cognitive function, performance, MRI and loss of the 2–5 A pathway deficit.

Chronic cerebral dysfunction (CCD) may occur in virtually any age group and is often associated with a post infectious disease episode thought to be viral in nature. Chronic cerebral dysfunction can occur following mononucleosis (1), brucellosis (2) or herpes-type 6 infections as well as other factors.

I have discovered and hereby disclose that a hyperactive or an aberrance in the 2–5 A synthetase/RNase L pathway exists in individuals having chronic cerebral dysfunction. This derangement is often accompanied by other biochemical and gross tissue anomolies such as cerebral lesions revealed by imaging as well as cognitive deficits such as loss of IQ and impaired attention and abstraction ability. Further, the natural killer cell function and NK cell phenotype are often unusual in CCD patients.

These disorders are effectively treated with dsRNA therapy which normalizes and favorably adjusts the 2-5 A synthetase/RNase L pathway and restores a dsRNA deficit in the patient. Improvement is seen on both the cellular and functional levels with memory and IQ values restored to near or at previous levels while exercise tolerance and oxygen consumption are increased. Patients having chronic cerebral dysfunction were assessed using various techniques and procedures as explained below.

Loss of Cognitive Functions

A variety of neuropsychologic instruments are available and I have used them to study and define a subset of patients with chronic cerebral dysfunctions. A typical test battery used has included the Wechsler Adult Intelligence Scale Revised (WAIS-R), the Wechsler Memory Scale, Immediate and Delayed (WMS); the Minnesota Multiphasic Personality Inventory (MMPI) and similar tests. Patients with CCD typically have test scores which are 2 standard deviations or more below the mean; some patients have an average of all scores which are one standard deviations or more below the mean and an occasional patient has multiple scores which are at least 4 standard deviations below the mean. Often I also observed "abstraction ability" and their performance on "set switching tasks" to also be impaired. Memory impairment seems to be secondary to a difficulty with attention and abstraction. Several patients were unable to perform such simple tasks as to balance their check books or place a key to the front door into the lock in the right configuration. These measurable and consistent cognitive deficits are unlikely to be caused by malingering or purely psychologic reasons since they often are associated with a downhill course in which the patient eventually becomes bed-ridden and almost moribund. I have also discovered a novel biochemical defect associated with this disease.

Magnetic Resonance Imaging of the Brain

Most of the patients from whom MRI scans were obtained complained of cognitive problems. The studies were generally performed using a 1.5 T superconducting Signa Magnetic Resonance Imager manufactured by the General Electric Company.

77% of the patients examined had abnormal MR scans: primarily punctuate areas of high signal intensity, and sometimes larger patchy areas of high signal intensity, consistent with focal edema and/or demyelination.

The subcortical white matter was affected most often, but lesions were seen in the deep white matter also.

There was a correlation between the anatomic area and the clinical presentation: for example, one patient with ataxia had lesions involving the cerebellum, nine patients with visual symptoms had lesions involving the occipital cortex, one patient with paresis had a lesion involving the contralateral internal capsule. In the several instances where MRI scans were repeated, lesions persisted until I intervened with dsRNA therapy.

NK (Natural Killer) Cell Phenotype and Function: An Immunological Derangement The NK cell phenotype and function are often unusual in patients with CCD. Phenotype: The usually predominant NKH1+T3 subpopulation (a subtyping of lymphocytes determined with monoclonal antibodies) can be diminished in patients with CCD, but are normal in control subjects including patients with situational depressions of a transient nature which are often improved by mood elevating drugs, change in environment, exercise, etc. Also, NK cell function (cytolytic activity against various target cell lines) was generously reduced in the CCD patients, but usually not in the control subjects. This defective cytolytic activity was particularly prominent after stimulation with interleukin-2, and when the target cell line was an (Epstein-Barr virus) EBV-infected cell line (LAZ 388). I have now performed the first serial studies on such patients and observed that the phenotypic and functional abnormalities in NK cells changed as the patients' clinical course improved following treatment with a source of exogenous dsRNA.

ing acquired immune deficiency or AIDs. Specimens from several patients I have studied indicate the intriguing possibility of "pseudotyping" as a means of spreading this disease. By pseudotyping, I refer, for example, to the coat of a herpes type 6 virus surrounding the genetic material for a retrovirus. This would give rise to a novel form of contagion where the infectious agent spreads epidemiologically through the population like a herpes virus but the genetic information being spread is actually that of a retrovirus. I have utilized a variety of genomic probes (4), coupled with serological and morphological considerations (5), to put forward this novel mechanism of biological spread leading ultimately to mental deterioration and morbidity.

I have also studied the 2-5 A/RNase L pathway in peripheral blood lymphocytes of 10 patients having CCD with both MRI lesions and neurological deficits associated with a decreased intelligence quotient. In the first phase of the study, I looked at the antiviral defenses of patients with only intelligence quotients (IQs) equal to or less than 105 whose prior occupation strongly suggested a higher premorbid IQ; in many patients I was able to locate tangible evidence revealing a higher IQ either months or years before the present cerebral illness.

Eight out of ten patients had a hyperactive or aberrant RNase L which caused an unnatural (unexpected) cleavage of ribosomal RNA in a typical polyacrylamide gel (PAGE) assay. Also, these eight patients had below normal levels of 2-5A synthetase before therapy. These patients responded most dramatically to dsRNA therapy in terms of improvement in IQ, MRI, etc., whereas the two patients without the biochemical defect had marginal responses.

TABLE 1

Coordinate Responses (Physiologic, Biochemical and Cognitive) In Patients With Cerebral Dysfunction With 2-5 A/RNase L Pathway Lesions A. Patients have decreased IQ. Following ds RNA (200-700 mg every 2 or 3 days given IV) IQ improves up to 50 points within 6 to 9 months.
B. MRI improves.
C. WAIS-R, WMS, MMPI improve, gradually normalizing within 9-18 months in many cases.
D. NM (Natural Killer) cell, immunological status improves.
E. Virologic "burden" decreases as evidenced by decrease in the number of peripheral blood cells containing infectious particles of herpes-6 virus.
F. Increased performance associated with improved exercise tolerance (prolonged ability to remain on treadmill) and improved oxygen consumption.
G. Correction of 2-5 A/RNase L pathway defect often is a leading indicator that precedes clinical response by 4-12 weeks or longer.

Antiviral Defenses and Virologic Studies

I have also observed that the majority of these patients are infected with herpes-6, a relatively new class of herpes virus only recently described (3), and never before associated with loss of mental capabilities. (Earlier studies found the virus in cancer patients.) The virus has been variously called HBLV (human B cell lymphocyte virus) or HHV-6 (human herpes virus-6). The main features of this virus are its icosahedral symmetry with about 162 capsomers and a lipid membrane. Infected cells develop into large refractive cells and some patients with CCD may have up to 20-30% or more of their circulating lymphocyte cells (a certain type of lymphocyte of bone marrow or thymus lineage) infected. Following dsRNA therapy for several months, the percentage of infected cells falls dramatically and is associated with clinical improvement in cognitive abilities. I have also found EB (Epstein-Barr) virus in many of these patients as well as a novel retrovirus similar(-though different genetically) to HIV, a retrovirus caus- Diagnosis is conveniently conducted from a sample of the patients blood to analyze the peripheral blood cells for enzymatically deficient 2-5'A using the procedures described by Carter et al in *The Lancet.* Jun. 6, 1987, p. 1286. The aberrance once noted is compared to the test results of otherwise healthy individuals, and is corrected by the exogenous administration of dsRNA, preferably a mismatched dsRNA, to improve the patient's clinical condition and restore cognitive abilities. During and at the conclusion of therapy, the patient is followed to ascertain his/her improvement on a cellular level, which usually precedes the clinical improvement by several weeks, and to determine the amount of dsRNA, if any, needed to maintain a normal 2-5'A synthetase/RNase L pathway and restore/maintain the patient's cognitive skills.

Diagnostic Procedures

The in vivo concentration of 2'-5'molecules in normal individuals and subjects with chronic cerebral dysfunction is assessed as follows: Ethanol-soluble fractions of patient samples (Ficoll-Hypaque-purified peripheral blood lymphocytes) were analyzed for their 2'-5'A content in 2'-5'A core-cellulose assays (affinity chromatography) with poly U-$\{^{32}P\}$-pCp. In this assay, the ability of 2'-5'A-activated RNase L to hydrolyze poly(U) is used to determine the concentration of functional 2'-5'A.

Reference values were established by testing 15 normal subjects with no recent history of viral infections as evidenced by lack of fever, absence of constitutional symptoms, rashes, etc. Concentrations of their lymphocyte 2'-5'A levels were determined using calibration curves obtained with authentic 2'-5'A molecules.

The dsRNA may be a complex of a polyinosinate and a polycytidylate containing a proportion of uracil bases or guanidine bases, e.g., from 1 in 5 to 1 in 30 such bases (poly I·poly($C_{4-29}x > U$ or G)).

The dsRNA may be of the general formula $rI_n \cdot r(C_{11-14},U)n$ or $rI_n \cdot r(C_{12},U)_n$. Other suitable examples of dsRNA are discussed below.

By "mismatched dsRNA" are meant those in which hydrogen bonding (base stacking) between the counterpart strands is relatively intact, i.e., is interrupted on average less than one base pair in every 29 consecutive base pair residues. The term "mismatched dsRNA" should be understood accordingly.

The mismatched dsRNAs preferred for use in the present invention are based on copolynucleotides selected from poly ($C_n$,U) and poly ($C_n$,G) in which n is an integer having a value of from 4 to 29 and are mismatched analogs of complexes of polyriboinosinic and polyribocytidilic acids, formed by modifying $rI_n \cdot rC_n$ to incorporate unpaired bases (uracil or guanidine) along the polyribocytidylate ($rC_n$) strand. Alternatively, the dsRNA may be derived from poly(I)·poly(C) dsRNA by modifying the ribosyl backbone of polyriboinosinic acid ($rI_n$), e.g., by including 2'-O-methyl ribosyl residues. The mismatched complexes may be complexed with an RNA-stabilizing polymer such as lysine and cellulose. These mismatched analogs of $rI_n \cdot rC_n$, preferred ones of which are of the general formula $rI_n \cdot (C_{11-14},U)_n$ or $rI_n 1 \cdot r(C_{29},G)_n$, are described by Carter and Ts'o in U.S. Pat. Nos. 4,130,641 and 4,024,222 the disclosures of which are hereby incorporated by reference. The dsRNAs described therein generally are suitable for use according to the present invention.

Other examples of mismatched dsRNA for use in the invention include:

poly (I)·poly ($C_4$,U)
poly (I)·poly ($C_7$,U)
poly (I)·poly ($C_{13}$,U)
poly (I)·poly ($C_{22}$,U)
poly (I)·poly ($C_{20}$,G)
poly (I)·poly ($C_{29}$,G) and
poly (I)·poly $C_p 23 G > p$ In addition, 2'-5'A concentration and molecular size may be quantitated by high pressure liquid chromatography (HPLC). Also, ribosomal RNA cleavage assays may be used to assess biological functionality (activity) of the 2'-5'A-synthesized by the patient in vivo or to determine the level of activated RNase L in patient samples. Peripheral mononuclear blood cells are the preferred cells for analysis.

Patients having chronic cerebral dysfunction are treated with intravenous infusions of 200 to 700 mg of $rI \cdot r(C_{11-14},U)$ as required, e.g., once a week to as often as daily and 2'-5'A enzyme levels increase in association with clinical improvement. The amount of dsRNA administered and the frequency of administration will be guided by the 2'-5'A synthetase levels measured in conjunction with the patient's clinical improvement, particularly return of cognitive functions. Amounts of dsRNA administered will provide a level of from 0.01 to 1,000 micrograms of dsRNA per milliliter of the patient's systemic blood circulation immediately following administration measured at a point distal from the point of infusion.

References (1) DuBois, E. E. et al, *Southern Med. Journal*, Vol. 77, pp. 1376 (1984)
(2) Imborlen, J. B. et al, *Archives Internal Medicine*, Vol. 103, pp. 406 (1959)
(3) Salahuddin, S. Z. et al, *Science*, Vol. 234, pp. 596 (1986)
(4) Josephs, S. F. et al, *Science*, Vol. 234, pp. 601 (1986)
(5) Ablashi, D. V. et al, *Nature*, Vol. 329, pp. 207 (1987).

What is claimed is:

1. A method of treating a patient suffering from chronic fatigue syndrome and having chronic cerebral dysfunction comprising administering to that person an amount of dsRNA sufficient to improve the patient's clinical condition.

2. A method of treating a patient suffering from chronic fatigue syndrome and having chronic cerebral dysfunction as evidenced by at least one of a partial loss in cognitive functions, impaired attention and abstraction ability, memory loss, and immunological derangement in natural killer cell function of phenotype or both or an enzymatic deficiency in the 2'-5'A pathway in the patient's peripheral blood cells, the method comprising administering to said patient an amount of dsRNA sufficient to improve the patient's condition.

3. The method of claim 2 in which the dsRNA is mismatched.

4. The method of claim 3 in which the mismatched dsRNA is a polyadenylic acid complexed with polyuridylic acid.

5. The method of claim 3 or 4 in which the mismatched dsRNA is a complex of polyinosinate and polycytidylate containing from 1 in 5 to 1 in 30 uracil guanidine bases.

6. The method of claim 5 in which the mismatched dsRNA is $rI_n \cdot r(C_{11-14},U)_n$ or the mismatched dsRNA contains regions of bond breakage and exhibits the favorable therapeutic ratio property of $rI_n \cdot r(C_{11-14},U)_n$.

7. The method of claim 3 in which the amount of mismatched dsRNA administered results in a level of from 1 to 1,000 micrograms of the mismatched dsRNA per milliliter of the patient's systemic blood circulation.

8. A method of treating a patient suffering chronic fatigue syndrome and having chronic cerebral dysfunction comprising administering to said patient from 200 to 700 mg of $rI \cdot r(C_{11-14},U)$ over a 1 to 7 day period and continuing said therapy until the patient's clinical symptoms have normalized as evidenced by improvement in the patient's cognitive functions.

9. The method according to claim 1, 2, 3 or 6 wherein the dsRNA is administered in an amount of from 200 to 700 mg per day or per week.

10. The method according to claim 1 or 2, wherein from 200 to 700 mg of $rI \cdot r(C_{11-14},U)$ is administered over 1 to 7 day period.

* * * * *